United States Patent [19]
Vick et al.

[11] Patent Number: 5,698,166
[45] Date of Patent: *Dec. 16, 1997

[54] SCENTED AIR FRESHENING DEVICE AND METHOD OF MAKING SAME

[75] Inventors: Doug M. Vick, Thomasville; James T. Baxter, Hahira; George S. Gibbs, Thomasville, all of Ga.

[73] Assignee: New Ideas International, Inc., Thomasville, Ga.

[*] Notice: The term of this patent shall not extend beyond the expiration date of Pat. No. 5,547,636.

[21] Appl. No.: 746,137

[22] Filed: Nov. 6, 1996

Related U.S. Application Data

[63] Continuation of Ser. No. 645,521, May 14, 1996, which is a continuation of Ser. No. 254,939, Jun. 7, 1994, Pat. No. 5,547,636, which is a continuation-in-part of Ser. No. 47,174, Apr. 12, 1993, abandoned, which is a continuation of Ser. No. 972,866, Nov. 3, 1992, abandoned, which is a continuation of Ser. No. 712,974, Jun. 10, 1991, abandoned, which is a continuation-in-part of Ser. No. 318,121, Mar. 2, 1989, abandoned.

[51] Int. Cl.[6] ............................................. A61L 9/04
[52] U.S. Cl. ............... 422/124; 261/30; 261/60; 261/DIG. 65; 55/279; 523/102; 428/905
[58] Field of Search ................................. 422/123, 124; 261/30, DIG. 65; 239/60; 55/279; 424/47, 76.9; 428/905; 523/102

[56] References Cited

U.S. PATENT DOCUMENTS

| | | | |
|---|---|---|---|
| 3,685,734 | 8/1972 | Pacioreck et al. | 239/56 |
| 3,804,796 | 4/1974 | Alexandre | 523/102 |
| 4,065,262 | 12/1977 | Petroff | 21/74 |
| 4,095,031 | 6/1978 | Engle | 523/102 |
| 4,118,226 | 10/1978 | Bourassa | 55/279 |
| 4,285,468 | 8/1981 | Hyman | 239/55 |
| 4,346,840 | 8/1982 | Gaiser et al. | 239/6 |
| 4,425,321 | 1/1984 | Jacquet et al. | 424/47 |
| 4,515,909 | 5/1985 | Sawano et al. | 523/102 |
| 4,563,333 | 1/1986 | Frigon | 422/122 |
| 4,604,114 | 8/1986 | Ward | 55/279 |
| 4,676,954 | 6/1987 | Wilson | 422/124 |
| 4,695,434 | 9/1987 | Spector | 422/116 |
| 4,696,844 | 9/1987 | Spector | 428/46 |
| 4,720,409 | 1/1988 | Spector | 428/46 |
| 4,735,358 | 4/1988 | Morita et al. | 239/1 |
| 4,741,944 | 5/1988 | Jackson et al. | 428/152 |
| 4,761,437 | 8/1988 | Christie | 523/102 |
| 5,019,434 | 5/1991 | Matsumoto | 428/35.7 |
| 5,087,273 | 2/1992 | Ward | 55/279 |
| 5,109,029 | 4/1992 | Malone | 521/79 |
| 5,240,653 | 8/1993 | Ramkisson | 261/99 |
| 5,258,051 | 11/1993 | Anderson | 55/279 |

*Primary Examiner*—Nina Bhat
*Attorney, Agent, or Firm*—Kennedy, Davis & Kennedy

[57] ABSTRACT

An air freshening device is made from a solution of a polymer and a fragrant material, which is applied to an air permeable substrate. A solid fragrant residue is formed on the substrate. A fragrant material diffuses from the residue for scenting flowing through and about the substrate. An attachment is provided for attaching the substrate to an air filter received in a forced air heating, ventilating, and cooling system.

20 Claims, 4 Drawing Sheets

SCENTED AIR FRESHENING DEVICE AND METHOD OF MAKING SAME

CROSS-REFERENCE TO RELATED APPLICATION

This is a continuation of application Ser. No. 08/645,521 filed May 14, 1996, a continuation of application Ser. No. 08/254,939 filed Jun. 7, 1994, issued Aug. 20, 1996 as U.S. Pat. No. 5,547,636, a continuation-in-part of our application Ser. No. 08/047,174 filed Apr. 12, 1993, now abandoned which was a continuation of Ser. No. 07/972,866 filed Nov. 3, 1992, now abandoned as a continuation of Ser. No. 07/712,974 filed Jun. 10, 1991, now abandoned as a continuation-in-part of application Ser. No. 07/318,121 filed Mar. 2, 1989, now abandoned.

TECHNICAL FIELD

The present invention relates to an air freshening device. More particularly, the invention relates to an air freshening device for scenting air in a mechanical forced air ventilation system.

BACKGROUND OF THE INVENTION

Releasing fragrance into ambient air has the effect of deodorizing and freshening the air. Compositions and devices for releasing fragrance over a long period of time are known. For example, U.S. Pat. No. 4,118,226 discloses placing a solid aromatic medium in a perforated case which in turn is placed in an air circulation system. U.S. Pat. No. 4,604,114 similarly discloses placing large solid rods of fragrant scented material in an air circulation system. U.S. Pat. No. 4,563,333 discloses a deodorizing fitting for an air filter in which a rectangular envelope of perforated cardboard with a deodorizing insert therein is adhered to the corner of the filter. U.S. Pat. No. 4,425,321 discloses deodorant compositions for treating textiles such as towels cause them to act as deodorants. U.S. Pat. No. 4,065,262 discloses utilizing a plurality of containers for holding an air freshening composition positioned in an air filter. U.S. Pat. No. 4,523,870 relates to an aroma dispensing cartridge placed in front of an air vent. U.S. Pat. No. 4,735,358 discloses fragrant material placed on a tape from which the material vaporizes when the tape is run across a tape head by drive means.

A problem exists, however, in that these prior art devices interfere with the flow of air through the circulation system. Furthermore, none of the inventions in these patents can be readily employed in a pre-existing filter system. Rather, specifically designed frames or casings must be used to hold the fragrant structures.

Another problem arises from the volatile nature of liquid fragrances. Fragrances for scenting air typically are liquid oils. Such fragrant oils are mixtures of many different chemicals. Most of the chemicals mixed into a fragrant oil are liquids, but some components are solid. A solvent is used to dissolve the components together to form a homogeneous fragrant liquid oil. The components have relatively high vapor pressures. By this is meant the fragrant liquids evaporate readily. Fragrant liquid oils are therefore not satisfactory for use in forced air ventilation systems carrying air at significant velocities. The present invention accordingly, addresses the conflicting problems associated with the deodorizing and scenting of air in forced air ventilation systems of entraining an effective amount of scent into the air while retaining sufficient longevity of its source.

There exists a need, therefore, for a scented air freshening device which may be used in a heating, ventilating, and cooling system for deodorizing and freshening air distributed by that system with nominal interference with the circulation of air through that system and while providing sufficient scenting of the air for an extended period. Accordingly, it is to the provision of such an improved air freshening device that the present invention is primarily directed.

SUMMARY OF THE PRESENT INVENTION

The air freshening devices and methods of producing them of the present invention meet this need in the art. The method of the present invention produces an air freshening device capable of deodorizing air in a forced air ventilation system upon attachment of the air freshening device to an air filter held therein. The method comprises the step of forming a solution of effective amounts of a fragrant material, a polymer and a volatile solvent. The solution is applied to a substrate through which air may pass. The solvent is allowed to evaporate to leave a dried fragrant polymeric residue on the substrate from which a fragrant scent is slowly released. The substrate, upon being attached to an air filter in a forced air ventilation system using attachment means, deodorizes and freshens the air forced through the filter.

A second method of the present invention produces an air freshening device for deodorizing air in a forced air ventilation system. With this second method a solid polymeric formulation is heated until liquified. The polymeric formulation is preferably a hot melt adhesive comprised of ethylene vinyl acetate. A fragrant liquid is added to the heated liquified polymeric formulation preferably in a ratio of between 1:4 and 4:1. The fragrant liquid and the heated liquified polymeric formulation are mixed together to form a heated solution. The heated solution is then applied to an air permeable substrate and allowed to cool to form a solid fragrant polymeric residue on the air permeable substrate from which a fragrant scent is slowly released. The air permeable substrate, upon being attached as an air freshening device to an air filter in a forced air ventilation system, emits a fragrance that deodorizes and freshens the air.

The present invention further provides a device for scenting air in a forced air ventilation system. The device comprises an air permeable substrate having interstices through which air may flow. A polymeric material coats the substrate in at least some of the interstices. The polymeric material has a liquid fragrant that may diffuse slowly from the coating and become entrained in the air flowing through and about the substrate. Means are provided for attaching the substrate to a face of an air filter through which air flows in a heating ventilation and cooling system. The air filter, upon being disposed in the forced air ventilation system with the substrate attached, releases a fragrance into the air flowing through the system.

DETAILED DESCRIPTION

Figure 1:
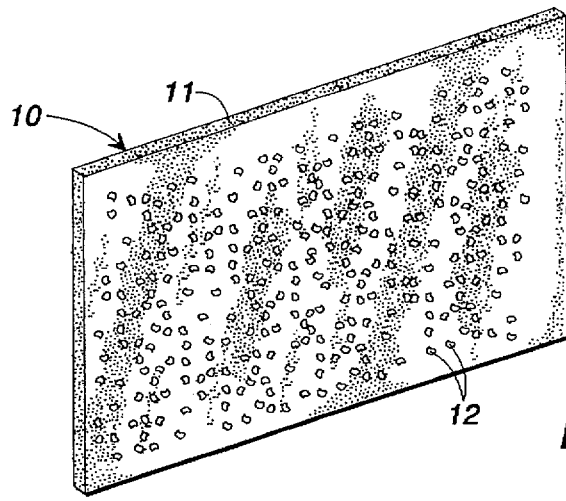
FIG. 1 is a perspective view of a fragrant air freshening device made in accordance with the present invention.

Referring now in more detail to the drawings in which like numerals indicate like parts throughout the several views, FIG. 1 illustrates a fragrant air freshening device 10 made in accordance with the present invention comprising an air permeable substrate 11. In the illustrated embodiment, the substrate 11 is a planar sheet of polyurethane foam (foam rubber). The substrate 11 supports a solid residue 12 which emits a fragrance, as discussed below. The solid residue 12 results from applying a fragrant solution to the substrate, which solution then dries. The fragrant solution is a homogeneous liquid mixture of a polymer, a fragrant liquid, and a solvent for the polymer and the fragrant liquid, which comprises a polymeric formulation. Allowing the solvent to evaporate leaves the fragrant solid residue 12 at various spots on the substrate 11. In the embodiment illustrated in FIG. 1, the solution migrates through the interstices of the substrate 12 and attaches to the walls of the air permeable passages in the material comprising the substrate.

Figure 2:
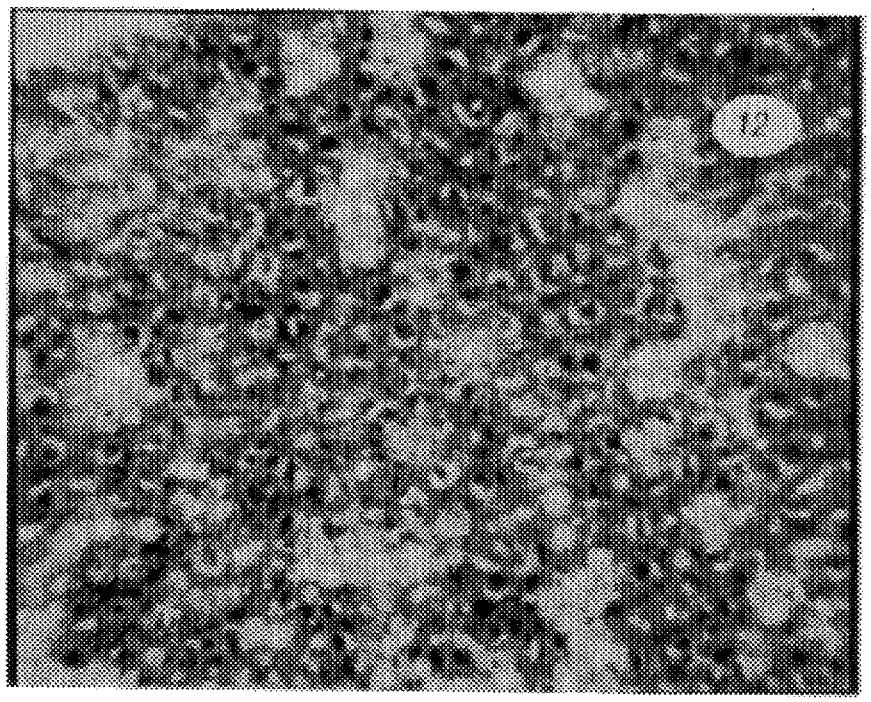
FIG. 2 is a microphotograph of an embodiment of the air freshening device illustrated in FIG. 1.

FIG. 2 is a microphotograph of an embodiment of the air freshening device 10 illustrated in FIG. 1, taken at 7 times power. This view illustrates the migration of the liquid mixture through and across portions of the substrate 11.

Figure 3:
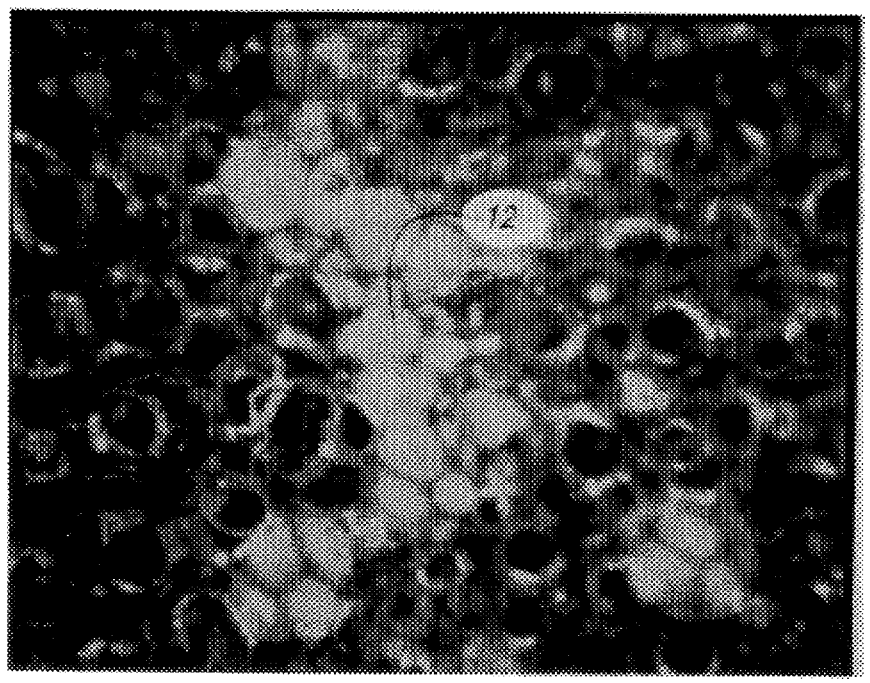
FIG. 3 is a second microphotograph of the embodiment shown in FIG. 2 at a higher magnification power.

FIG. 3 is a microphotograph at 20 times power of the embodiment of the air freshening device 10 shown in FIG. 2. This view more readily shows that some of the air permeable passages in the substrate 11 are blocked and occluded by the dried residue 12. In other passages, the walls are only coated with the dried residue 12. The substrate 11, however, remains substantially air permeable for passage of air when the device 10 is installed in a heating, ventilating, and cooling system, as discussed below.

Figure 4:
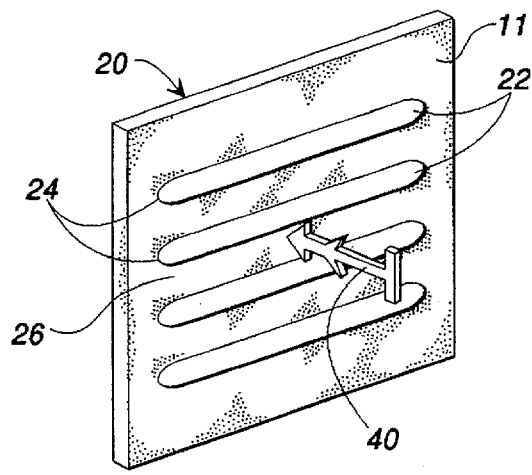
FIG. 4 is a perspective view of a second embodiment of a fragrant air freshening device made according to a preferred method of the present invention.

FIG. 4 is a perspective view of a second embodiment of a fragrant air freshening device 20 which comprises the same air permeable substrate 11 as before. In this embodiment the substrate 11 supports several spaced-apart fragrant beads 22 which result from mixing a melted polymeric formulation, sometimes referred to herein as a polymer, and a fragrant liquid together as a solution. The beads 22 are applied as a heated solution that sets quickly upon cooling to form a solid residue which emits a fragrance slowly into the air. The beads 22 of the solid residue are preferably spaced apart on the substrate 11 that measures approximately 6 inches wide by 6 inches long by one-fourth inch thick. The beads 22 are approximately one-half inch in diameter. Satisfactory longevity of continuing emission of fragrance from the air freshening device 20 is obtained with the use of approximately 45 grams of the solution being applied to the substrate 11.

Figure 5:
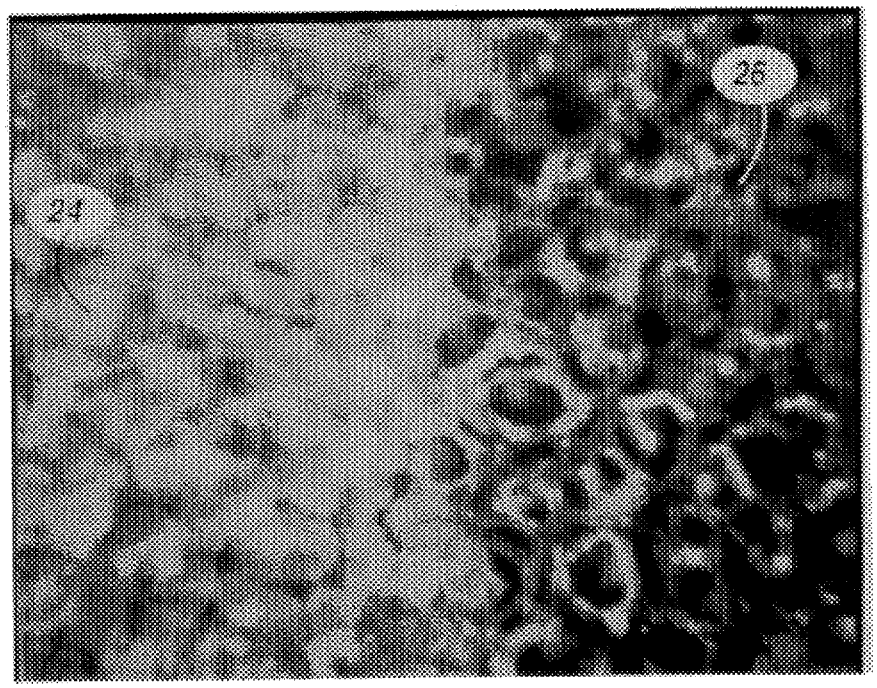
FIG. 5 is a microphotograph of an embodiment of the air freshening device illustrated in FIG. 4.

FIG. 5 is a microphotograph of the embodiment of the fragrant air freshening device 20 illustrated in FIG. 4. The beads 22 of the solid fragrant residue are held on the substrate 11. With a short set time, the solution does not substantially migrate through the substrate 11. The solid residue 22 plugs the interstices and air permeable passages in a portion of the substrate 11 to which it is applied. Thus the substrate 11 has air permeable portions 24 and blocked portions 26 closed by the solid residue 22.

The air freshening devices 10 and 20 of the present invention accordingly have an air permeable substrate 11 that bears evaporative solid materials 12 and 22 from which fragrant material diffuses and evaporates for scenting air flowing through the substrate, such as in a forced air heating, ventilating, and cooling system.

Figure 6:
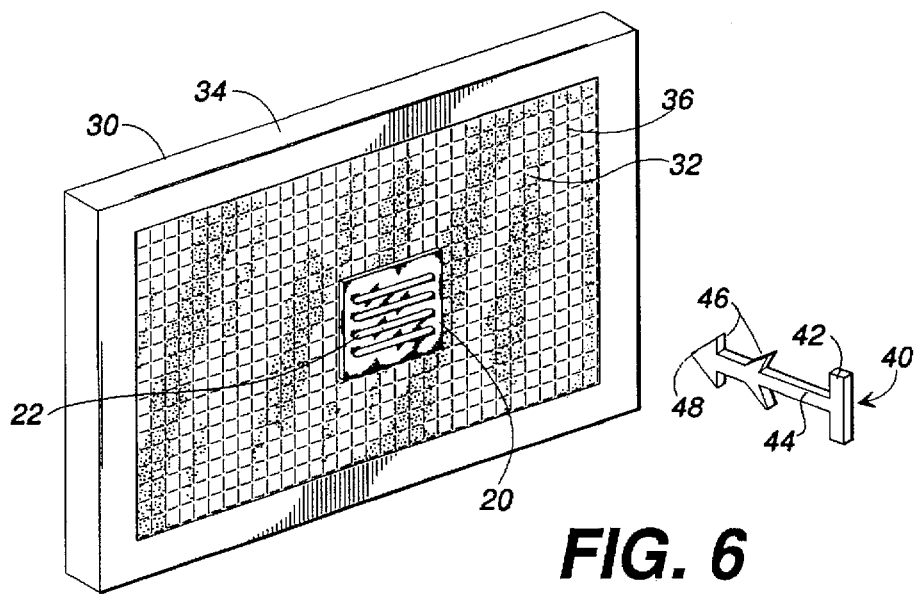
FIG. 6 is a perspective view of the air freshening device illustrated in FIG. 4 attached to a conventional air filter.

FIG. 6 illustrates a conventional air filter 30 of a commercially available type typically provided for use in a receiving slot (not illustrated) of a forced air heating, ventilating and cooling system. The air filter 30 is conventional, being comprised of fibrous filtering material 32, such as a textile material or other woven fibers that arrest particles in the interstices of the material 32, and a rigid or semi-rigid frame 34 about the periphery of the material 32 for holding the filtering material in position. Typically a mesh 36 is attached to the frame 34 for further maintaining the filtering material 32 within the frame.

FIG. 6 further illustrates the air freshening device 20 of the present invention attached to the filter 30. Exploded from the air freshening device 20 is a device 40 used for attaching the fragrant air freshening device 20 to the air filter 30. In the illustrated embodiment, the device 40 comprises a barbed shaft having a stop 42 at a first end of an elongated shaft 44. A series of barbs 46 extend outward of the elongated shaft 44 at a distal end 48. The barbed shaft 40 is cast with low cost plastic. Other attachment devices could be used, such as a length of wire having hooks at distal ends which engage the substrate 11 and the mesh 36 of the filter 30.

In mounting the device 10, 20 to an air filter 30, the barbed shaft 40 is pushed through the substrate 11. The barbs 46 engage the fibers 32 of filter 30. The stop 42 bears against the substrate 11. The air filter 30 is placed in a receiving slot of a heating, ventilation and cooling system. Fragrant scent diffuses from the solid residue into the air flowing through the substrate for deodorizing and freshening air delivered by the forced air system with the scent. The device 10, 20 can be used in an enclosed space for freshening air, such as placing the device under a seat in an automobile or truck.

Methods and compositions for producing the air freshening devices 10, 20 are described below. The present invention provides a first method of producing an air freshening device that can be attached to an existing air filter in an air filtration system or can be placed in an enclosed space. The steps of this method include mixing effective amounts of a fragrant material, a polymer, and a solvent for the fragrant material and the polymer. The solvent dissolves the polymer and the fragrant material which then mix together to form the viscous solution of a homogeneous liquid. An effective amount of the fragrant material is dependent upon the particular fragrant material used and the polymer that is the carrier for the fragrant material. The fragrant material must evaporate from the surface of the polymer which carries the fragrant material and the fragrant material must release at a low rate to provide longevity of use of the scenting device.

The solution is next applied to the substrate 11 through which air can pass. Allowing the solvent to evaporate leaves a fragrant solid residue 12 on the substrate 11. The solvent is preferably volatile to facilitate drying the solution to form the residue 12. The substrate 11 may then be attached to an existing air filter 30 for scenting air passing through the filter. The preferred means of attachment is the barbed shaft 40, although other means for attaching the substrate to an existing air filter can be used. As discussed above, the substrate 11 to which the solution is applied is preferably a piece of polyurethane foam rubber, but can be other fibrous filter material, a mesh material, or other porous or perforated substrate through which air may pass.

The fragrant material typically is supplied in liquid form, as most fragrances are oily liquids. The fragrant material may be selected from among commercially available fragrances such as honeysuckle fragrance or pine fragrance available from Flavor & Fragrance Specialties of Franklin Lakes, N.J. or Aromatic, Flavors & Fragrances of Marietta, Ga. The fragrant oils have relatively high vapor pressures, which means that they evaporate quickly. The polymer performs the functions of holding the fragrant liquid on the substrate 11 and of controlling the release of the fragrant material through evaporation into the air in the heating, ventilating, and cooling system. The polymer provides long chain molecules for binding the fragrant molecules in the interstices of the polymers. As the fragrant material evaporates from and near the surface of the solid residue that carries the fragrant material, more fragrant material diffuses through the solid residue to the surface.

The polymer used in the first method of producing an air freshening device is preferably hydroxypropylcellulose (HPC). Since some fragrances tend to release too fast from hydroxypropylcellulose, to reduce their release rates, a mixture of hydroxypropylcellulose and polyvinylpyrrolidone vinyl acetate (PVA) may be used. The ratio of polymers may range from about 4:1 to about 1:4 although 2:1 is preferred. Thus different ratios of the blend of these polymers control the release rate for a given fragrance. The PVA tends to hold the fragrance tighter in the solid residue carrier than does the HPC. Thus, a more volatile fragrance is preferably used with a HPC and PVA mixture having a ratio closer to the 1:4 portion of the range. A fragrance with a lower vapor pressure is preferably used with a mixture closer to the 4:1 ratio. However, the air freshening devices made with the HPC polymer alone have commercial advantages over the devices made with the HPC and PVA blend in which the dried residue softens and pools during storage.

The first method mixes together the polymeric liquid and the fragrant liquid. The ratio of the effective blends of polymer and fragrant liquid ranges from about 1:4 to about 4:1 by weight. A ratio of 1:1 however is preferred because a constant ratio for each commercialized device simplifies manufacturing of devices using different fragrances. The fragrances used commercially in the devices 10 are those that blend at about the 1:1 ratio into the polymer and release slowly for longevity of the air freshening device. During manufacturing, changing from one fragrance to another is simplified; no change to the blend ratios is necessary.

A second method of producing an air freshening device 20 includes the steps of heating a solid polymeric formulation until it melts, adding a fragrant material to the melted polymeric formulation, mixing until the mixture is homogeneous, applying the mixture to a substrate through which air may pass, and allowing the mixture to cool to leave a fragrant residue on the substrate.

The polymeric formulation used with this method is preferably a hot melt adhesive, and is preferably one that includes ethylene vinyl acetate. Regardless of the polymeric formulation used, it must be miscible with the fragrant liquid so as to form a homogeneous heated solution to form a homogeneous solid that carries the fragrant material and slowly releases the fragrant material in ambient air. It is preferred that the fragrant liquid and the liquified hot melt adhesive be mixed in a closed chamber. The ratio of the fragrant liquid and the hot melt adhesive varies depending upon how readily the fragrant material diffuses or evaporates from the carrier polymer, i.e., on its particular vapor pressure. As discussed herein, some polymers bind the fragrant material more tightly than others. For example, vanilla fragrance generally releases more slowly than does cinnamon or wildflower. In the commercial practice of the second method the ratio of the fragrant liquid to the polymeric formulation is preferably 3:2 which simplifies manufacturing as discussed above by using only the various fragrances that have vapor pressures which blend and have sufficient longevity at about this particular ratio.

The hot melt glue used in the present invention meets a number of key criteria. Hot melt glue preferably does not melt at temperatures below 150° F. This enables products embodying the invention to be shipped and stored even though temperatures in truck vans and warehouses often reach high levels. The polymer usually maintains uniform viscosity with the different fragrances while heating during manufacturing of the scenting device. The polymers used should also set rapidly, preferably within a 5° F. reduction in temperature from the melting temperature. In the liquified form, the solution of the polymer and the fragrant material should not significantly bleed through or migrate in the substrate. The polymer preferably releases the fragrant material at a substantially constant rate. Also, the polymer should release as much of the fragrant material as possible during the operational life of the air scenting device. To this end, a preferred hot melt adhesive is No. 7430 available from H. B. Fuller.

This particular hot melt adhesive is a polymeric formulation having low viscosity, ranging from 5600 centipoise at 250° F. to 660 centipoise at 375° F. At 300° F., the viscosity is 2200 centipoise; at 325° F., the viscosity is 1385 centipoise; at 350° F., the viscosity is 935 centipoise.

Surprisingly, the liquified hot melt adhesive and the volatile liquid fragrance readily mix together to form the solution of heated homogeneous liquid without the heat of the liquified hot melt adhesive driving off the volatile fragrance. This is surprising because of the significant difference between the melting temperature of the hot melt adhesive and the lower vaporization temperature of typical fragrances. Hot melt adhesives rapidly become liquified at temperatures of approximately 160° C. Fragrant compounds are typically liquid mixtures that rapidly vaporize at approximately 100° C. Surprisingly, mixing these fragrant liquids with liquified hot melt adhesive does not drive off the fragrant compound with resulting loss of fragrance. It is believed that the fragrant liquid readily solubilizes with the hot melt adhesive and thus is incorporated into the interstices of the long chain polymer.

A test was conducted to determine the amount of fragrance lost when mixed with liquified hot melt adhesive. 100 g of the hot melt adhesive was placed in an open beaker. The hot melt adhesive was heated to 170° C. and then cooled to 130° C. 99.2 g of a fragrant compound was added to the liquified hot melt adhesive. The temperature of the materials in the beaker fell to 70° C. and the consistency became semi-solid. The materials were stirred in the presence of heat until homogeneous at 90° C. The mixture was left in the open beaker and allowed to cool for 7 hours before samples were taken. It was determined that only approximately three-tenths of one percent (0.3%) of the fragrant compound had evaporated from the hot melt adhesive.

In both of the above described methods, the evaporative fragrant solution applied to the substrate 11 and the resulting evaporative fragrant solid 12 and 22 are preferably homogeneous and single phase. By this is meant the solution and the solid each have uniform properties through the material. The polymer, the liquid fragrance, and the solvent have common polarity characteristics. Unlike polarity characteristics among the polymer, the fragrant liquid, and the solvent would resist these components forming the homogeneous liquid solution and the resulting homogeneous evaporative solid. In method I, the HPC is substantially polar. The solvent used to dissolve the HPC and the fragrant liquid likewise is polar. A preferred solvent is ethyl alcohol. In method II, the ethylene vinyl acetate typically used in hot melt adhesives is highly non-polar. The fragrant liquid used in the device must likewise be non-polar to blend and mix homogeneously. A preferred non-polar solvent for the fragrant liquid in method II is diethyl phthalate.

The following example demonstrates the non-miscible character of components with unlike polar characteristics. A peach fragrant liquid containing dipropylene glycol, a polar solvent had been prepared for use in method II. Three samples of the fragrance were mixed into a heated liquified ethylene vinyl acetate hot melt adhesive. Two samples A and B each included a different solubilizer (unidentified by the supplier of the peach fragrant liquid) and sample C did not. The samples were made to determine whether this particular peach fragrance could be used with method II. All samples were 63% fragrance to 37% adhesive, by weight.

It was determined that Sample A was not miscible; that Sample B was not miscible with excessive foaming upon addition of the fragrant liquid to the hot melt adhesive; and that Sample C, although initially believed miscible was found to be not miscible due the hardness and inflexibility of the solid residue.

The following are illustrative examples of the two methods for producing the air freshening devices 10 and 20 of the present invention.

Example I (Method I)

2896 g of honeysuckle fragrant liquid is dissolved in 6037 g of ethyl alcohol. 1934 g of hydroxypropylcellulose and 1934 g of 50% polyvinylpyrrolidone vinyl acetate solution in ethyl alcohol is added to the solution with stirring. The resulting mixture is stirred three hours at room temperature in order to completely dissolve the hydroxypropylcellulose. The solution is then pumped onto a piece of polyurethane foam (foam rubber) such as 6"×6"×¼" or 3"×3"×¼. After approximately four hours at room temperature the solvent evaporates from the solution and a solid fragrant residue remains on the fibers of foam rubber so that the air passages are not restricted. The fragrant residue causes minimum change in the velocity of the air passing through the foam rubber while scenting the air passing therethrough.

Example II (Method II)

27 g of hot melt adhesive (ethylene vinyl acetate copolymer) and 3 g of polybutene plasticizer is heated until melting occurs (about 250° F.). 45 g of honeysuckle fragrant liquid is warmed at room temperature to between about 70° F. and 80° F. Such pre-warming facilitates the blending of the liquid fragrance and the liquified hot melt adhesive. The warm liquid fragrance is added to the melted hot melt adhesive and stirred until a homogeneous mixture results. This mixture is poured onto a piece of polyurethane foam (foam rubber). Within five minutes the mixture cools and a solid fragrant residue remains on the piece of foam rubber. The fragrant residue causes nominal change in the velocity of air passing through the foam rubber while scenting the air.

Example III (Method II)

30 g of hot melt adhesive (ethylene vinyl acetate copolymer) is heated until melting occurs (about 250° F.). 45 g of honeysuckle fragrant liquid is warmed at room temperature to between about 70° F. and 80° F. The warm fragrant liquid is added to the melted hot melt adhesive and stirred until a homogeneous mixture results. This mixture is poured as a series of spaced-apart beads onto a piece of polyurethane foam (foam rubber). Within five minutes the mixture cools and a solid fragrant residue remains on the piece of foam rubber. The fragrant residue causes nominal change in the velocity of air passing through the foam rubber while scenting the air.

The operation of the present invention involves the dynamic evaporation of fragrance materials from an exposed surface of the carrier polymer and replenishment migration of the fragrance through the carrier to the surface for evaporation. The device 10, 20 of the present invention balances the conflicting needs of a fragrance emission sufficient to scent air with the requirement for a controlled rate to provide for the longevity of the emission during a typical operation, such as the four week period generally recommended for change-out of HVAC filters. Further, the carrier polymers vary in the percentage of fragrance that migrates and evaporates from the carrier. A carrier with a high migration percentage would reduce the volume of fragrance material necessary to be in the homogeneous solid, resulting in lower material cost.

Figure 7:
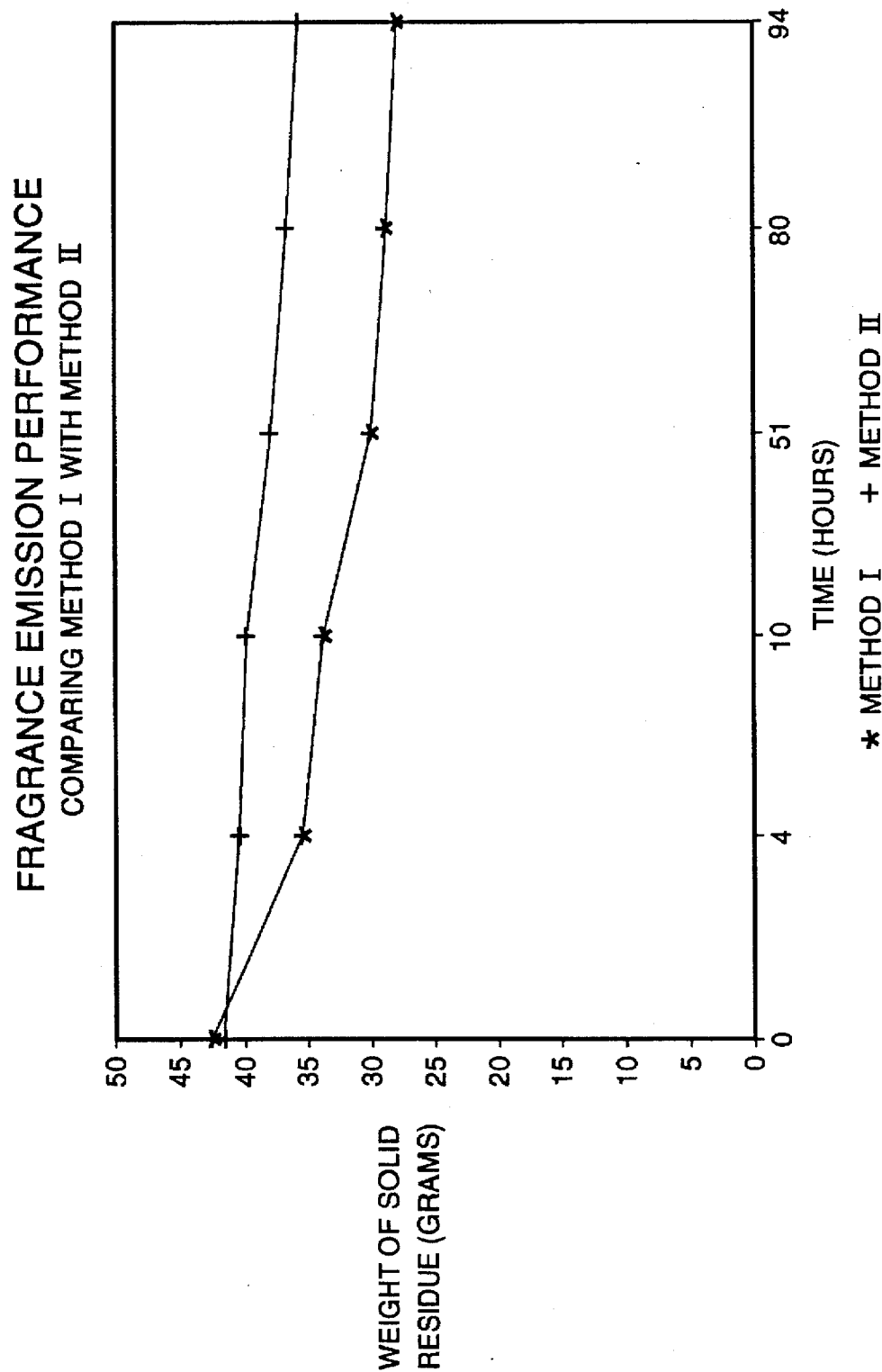
FIG. 7 is a graph comparing the performance of air freshening devices made according to the present invention.

FIG. 7 illustrates the general fragrance emission performance of freshening devices 10, 20 made according to method I and method II. An air freshening device 10 and an air freshening device 20 where made according to the methods discussed above. The device of method I used an HPC polymer while the device 20 of method II used a hot melt adhesive polymeric formulation that included ethylene vinyl acetate. The polymers and the liquid fragrance were mixed in a 1:1 ratio. The substrates 11 were weighed prior to applying the liquid mixtures of polymer and fragrant material. After allowing the solvent to evaporate and the hot melt adhesive to set, the substrates 11 with the dried residue 12, 22 were weighed. The substrates were placed in a test apparatus in which a fan pulls air continuously through the substrates 11 during the test. At several intervals, the devices 10, 20 were removed from the test apparatus and weighed. The difference in weights shows the amount of fragrant material lost to evaporation during the interval as reported in the following Table I.

TABLE I

FRAGRANCE EVAPORATION TEST

| Interval (hours) | Weight of Solid Residue (Device 10) (grams) | Weight of Solid Residue (Device 20) (grams) |
| --- | --- | --- |
| 0 | 42.5 | 41.7 |
| 4 | 35.4 | 40.4 |
| 10 | 33.9 | 40.1 |
| 51 | 30.3 | 38.4 |
| 80 | 29.1 | 37.1 |
| 94 | 28.3 | 36.1 |
| Total weight loss | 14.2 | 5.6 |

The data in Table 1 is plotted on the graph shown in FIG. 7 which illustrates the general fragrance emission performance of air freshening devices 10, 20 made according to method 1 and method 2. Generally, the air freshening device 10 made in accordance with method I releases a greater amount of fragrance during the initial period of use than during subsequent periods. The performance of the air freshening device 20 made in accordance with method II had more uniform emission of the scent over the operational life of the air freshening device.

The total weight loss for device 10 during the four day period was 14.2 grams. The total weigh loss of device 20 during the four days was 5.6 grams. The fragrant liquid and the polymer were mixed at a 1:1 ratio. Accordingly, the initial amount of solid residue 12 in the device 10 totaled 21.25 grams while the initial amount of solid residue 22 in the device 20 totaled 20.85 grams. The percent loss can be determined by dividing the total weight loss during the period by the initial fragrance weight in the dried residue:

Device 10 percent weight loss $$14.2 \div 21.25 \times 100 = 66.8\%$$

weight loss during four day continuous operation test
Device 20 percent weight loss $$5.6 \div 20.85 \times 100 = 26.9\%$$

weight loss during four day continuous operation test

These computations show that the device 10 of method 1 had a 66.8% weight loss of fragrant material in the four day period while the device 20 of method 2 had a 26.9% weight loss of fragrant material for the same period. The polymer of hot melt adhesive accordingly provided a more uniform and slow release of the fragrant materials, thereby leading to a lengthened useful life of the device 20 in a heating, ventilating, and cooling system. The reduction or cessation of scenting the air serviced by such system acts as a reminder to change the air filters on a periodic basis.

It is thus seen that an improved air freshening device and methods of making such device are now provided. While this invention has been described in detail with particular reference to the preferred embodiment thereof, it should be understood that many modifications, additions and deletions may be made thereto without departure from the spirit and scope of the invention as set forth in the following claims.

We claim:

1. A device for scenting air in a forced air ventilation system, comprising:
   an air permeable substrate having a plurality of interstices therein for communicating air through the substrate;
   a solid fragrant residue formed on the substrate and permeating into at least some of the substrate interstices so that a fragrant scent slowly releases when the substrate having the solid fragrant residue formed thereon is positioned in a forced air ventilation system;
   and an attacher for interconnecting the substrate having the solid fragrant residue formed thereon to a face of an air filter in a forced air ventilation system.

2. The device as recited in claim 1, wherein the solid fragrant residue is a residue of a substantially homogeneous solution applied to the substrate, which contains a solid dissolved in a solvent and an effective amount of a fragrant material.

3. The device as recited in claim 2, wherein the solid fragrant residue is formed by evaporating at least some of the solvent from the substantially homogeneous solution on the substrate.

4. The device as recited in claim 2, wherein the solid dissolved in the solvent is a polymeric material.

5. The device as recited in claim 4, wherein the polymeric material is selected from the group consisting of hydroxypropylcellulose, polyvinylpyrrolidone, and mixtures thereof.

6. The device as recited in claim 5, wherein the fragrant material is a fragrant oil.

7. The device as recited in claim 6, wherein the effective amount of the fragrant material being present in the substantially homogeneous solution in a ratio (by weight) of solid to fragrant material ranging from about 1:4 to 4:1.

8. The device as recited in claim 7, wherein the solvent comprises ethyl alcohol.

9. The device as recited in claim 2, wherein the fragrant material comprises a fragrant oil.

10. The device as recited in claim 9, wherein the fragrant oil being present in the substantially homogeneous solution in a ratio (by weight) of solid to fragrant oil ranging from about 1:4 to 4:1.

11. The device as recited in claim 2, wherein the solvent comprises ethyl alcohol.

12. The device as recited in claim 1, wherein the solid fragrant residue is formed on the substrate by:
    applying a substantially homogeneous solution containing a meltable solid and an effective amount of a fragrant material to the substrate;
    and cooling the homogeneous solution on the substrate.

13. The device as recited in claim 12, wherein the meltable solid is a polymeric material.

14. The device as recited in claim 13, wherein the effective amount of the fragrant material being present in the substantially homogeneous solution in a ratio (by weight) of solid to fragrant material ranging from about 1:4 to 4:1.

15. The device as recited in claim 12, wherein the polymeric material is a hot melt adhesive.

16. The device as recited in claim 15, wherein the hot melt adhesive comprises ethylene vinyl acetate.

17. The device as recited in claim 12, wherein the effective amount of the fragrant material being present in the substantially homogeneous solution in a ratio (by weight) of solid to fragrant material ranging from about 1:4 to 4:1.

18. The device as recited in claim 12, wherein the fragrant material is a fragrant oil.

19. The device as recited in claim 18, wherein the effective amount of the fragrant oil being present in the substantially homogeneous solution in a ratio (by weight) of solid to fragrant material ranging from about 1:4 to 4:1.

20. The device as recited in claim 19, wherein the meltable solid is a polymeric material.

* * * * *